United States Patent [19]

Himpens

[11] Patent Number: 4,603,699
[45] Date of Patent: Aug. 5, 1986

[54] APPARATUS AND METHOD FOR MEASURING OSMOTIC PRESSURE IN SITU

[76] Inventor: Jacques M. Himpens, P.O. Box 608, North White Plains, N.Y. 10603

[21] Appl. No.: 673,290

[22] Filed: Nov. 20, 1984

[51] Int. Cl.$^4$ ................................................. A61B 5/00
[52] U.S. Cl. ................................... 128/632; 128/637; 128/673; 128/748; 73/64.3
[58] Field of Search ............................... 128/673–675, 128/748, 637, 632, 635; 73/64.3

[56] References Cited

U.S. PATENT DOCUMENTS

| 2,840,069 | 6/1958 | Squire et al. | |
|---|---|---|---|
| 3,635,075 | 1/1972 | Gilbert | 73/64.3 |
| 4,028,931 | 6/1977 | Bisera et al. | 73/64.3 |
| 4,150,564 | 4/1979 | Barlow et al. | 73/64.3 |
| 4,170,895 | 10/1979 | Kliger | 73/64.3 |
| 4,245,495 | 1/1981 | Kakiuchi et al. | 73/64.3 |
| 4,305,823 | 12/1981 | Batzer et al. | 210/500.2 |
| 4,403,984 | 9/1983 | Ash et al. | 128/632 X |
| 4,431,009 | 2/1984 | Marion et al. | 128/674 X |
| 4,475,556 | 10/1984 | Reiff | 128/673 |
| 4,538,616 | 9/1985 | Rogoff | 128/632 |

OTHER PUBLICATIONS

An Intravascular Protein Osmometer, by John W. Henson and Robert A. Brace, American Journal of Physiology, 244 (Heart Circ. Physiol., 13): H726–H729, 1983.

Primary Examiner—Kyle L. Howell
Assistant Examiner—John C. Hanley
Attorney, Agent, or Firm—Lane and Aitken

[57] ABSTRACT

A multiple-lumen Swanz-Ganz catheter is disclosed wherein said first and second lumens are connected to an osmotic pressure sensor and a third lumen is connected to a hydrostatic pressure sensor. First and second lumens are fluidly continuous, connected through six hollow fibrils. Pressure in the first and second lumens is added to the pressure of the third lumen to determine colloid osmotic pressure.

The fibrils are made of a cellulose acetate material permeable to substances having a molecular weight less than 30,000 and filled with nylon filaments. The fibrils are exposed to the bloodstream through a port in the catheter which also provides an external opening for the third lumen. Fluid in the fibrils is pulsed to remove debris from the surfaces of the fibrils 16. The surfaces of the fibrils are also flushed periodically with physiological saline solution from the third lumen to prevent obstruction. The catheter is held in place by a flotation balloon.

7 Claims, 3 Drawing Figures

APPARATUS AND METHOD FOR MEASURING OSMOTIC PRESSURE IN SITU

BACKGROUND OF THE INVENTION

1. Field of the Invention

The present invention relates to the monitoring of haemodynamic parameters. More particularly, the present invention provides an apparatus and method for monitoring patients' osmotic or oncotic pressure in situ.

2. Background of the Invention

Apparatus for measuring hydrostatic pressure in situ is well known. A catheter is commonly inserted into a central vein or into a pulmonary artery for this purpose.

However, fluid exchanges occurring between the blood stream and body tissues which produce conditions such as pulmonary edema are governed by osmotic pressure effects, particularly colloid osmotic pressure (COP), as well as hydrostatic pressure. Monitoring these exchanges in critically-ill patients and high-risk surgical patients is particularly important, but in these cases it is also very important to minimize the effect of such monitoring on the patient's physiological condition. For example, COP monitoring can be valuable in the management of shock, myocardial infarction, serious burns, malnutrition, and hepatic or renal failure cases, but the need to minimize the risk to these patients induced by such monitoring is self-evident.

Intravascular osmotic pressure can be intermittently determined by measuring molar freezing point depression or by measuring the protein content of a blood sample. However, either measurement involves time delays and repeated blood withdrawals that make such a method cumbersome and ill-suited to monitoring critically ill patients. Furthermore, measurement of freezing point depression indicates only total osmotic pressure, and the determination of COP by measurement of the protein content of blood is very sensitive to laboratory errors in protein measurement. The Landis-Pappenheimer formula on which the latter approach is based is a species-specific exponetial function of blood protein for a given body temperature:

$$COP = xC + yC^2 + zC^3$$

where:

C = total protein (grams/dl)

x, y, z = temperature-variable constants Further discussion of this method can be found in the American Physiological Society's *Handbook of Physiology* (Washington, D.C., 1963) Circulation Vol. 2, pp 961–1034.

Continuous extracorporeal monitoring of COP can be achieved by shunting the bloodstream through external disc or needle osmomitors. These devices are described by Weil et al in U.S. Pat. No. 4,028,931 and by Kakuichi et al in U.S. Pat. No. 4,245,495, respectively. However, the shunting of the bloodstream through external devices is cumbersome at best. For critically-ill patients this shunting often represents an unacceptable risk, particularly when blood pressure or blood volume is low for any reason.

Additionally, it has been suggested that pulmonary edema can be produced by local changes in COP that are not readily observable elsewhere in the patients' system. Thus, the location at which COP is measured has a potentially significant effect of the usefulness of the measurement. This further complicates methods of COP determination requiring either shunting of the bloodstream or repeated blood withdrawal.

An experimental single-lumen device for short-term intravascular monitoring of COP in heparinized animals was disclosed by Henson et al, Am. J. Physiol. pp H726–H729 (1983). The device consists of a single catheter lumen terminated by a closed-end semipermeable tube and by a pressure sensor, respectively. This device is not suitable for use in human subjects, nor is it suited for use in continuous monitoring of COP in situ.

SUMMARY OF THE INVENTION

Apparatus for measuring osmotic pressure in accordance with the present invention comprises multi-lumen catheter means for insertion in a patient's bloodstream. The catheter has a distal catheter port through which one or more tubes of semi-permeable material in the catheter can be exposed to the patients' bloodstream. The tubes fluidly connect a first lumen to a second lumen. Respective ends of the tube or tubes are connected to the first and second lumens in airtight, watertight seals. The first lumen is connected to a pressure sensor adapted to measure the pressure of fluid in that lumen. While in situ the tube or tubes may be scrubbed by ultrasonically pulsing the fluid therein, or flushed by fluid from a third lumen to remove debris.

The catheter is inserted in the bloodstream and secured at a predetermined point. The equilibrium pressure of a physiologically normal solution filling said tube or tubes and said first and second lumens is then periodically measured and added to the concurrent hydrostatic pressure of the blood at that point in the blood stream to determine the intravascular colloid osmotic pressure at that point.

BRIEF DESCRIPTION OF THE DRAWING

The nature and advantages of the present invention will be more clearly understood when the detailed description of the preferred embodiment given below is considered in conjunction with the drawings, wherein.

DETAILED DESCRIPTION OF THE PREFERRED EMBODIMENT

Figure 1:
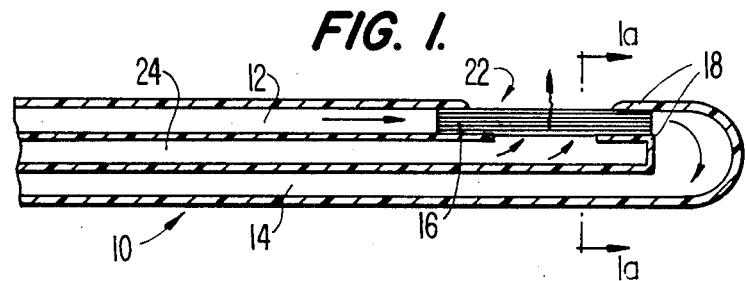
FIG. 1 is a cross section view of catheter means for apparatus in accordance with the present invention.

With reference to FIG. 1, the tip of a multiple-lumen polyvinyl chloride (PVC) catheter 10 with a diameter in the range of 18 Ga to 8 French for use in Swanz-Ganz catheter insertion apparatus is shown. The catheter has a first lumen 12 that is fluidly connected to a second lumen 14 through six hollow thread-like fibrils 16 that are 3 cm. long and have an outer diameter of 275 $\mu$m and an inner diameter of 40 $\mu$m. The ends of the fibrils 16 are sealed to each lumen, respectively, in an airtight and watertight seal 18. The fibrils 16, however, are semi-permeable cellulose acetate membrane tubes that are permeable to substances having a molecular weight of less than 30,000. Each fibril 16 is filled with nylon filaments 20, as in a Wick catheter. These nylon fibers 20 provide a desirable surface area to fluid volume relationship for the tubes, reducing the amount of fluid transferred out of the fibrils, and also provide internal support for the tubes, minimizing the distortion of the tubes produced by pressure differences acting across the membrane wall of each fibril 16.

The walls of the fibrils 16 are exposed through a catheter port 22 at the distal end of the catheter 10. The catheter port is one centimeter long. A third lumen 24 also opens externally through the port 22 so that fluid leaving the third lumen 24 washes across the fibrils 16. The catheter 10 also includes a balloon 26 near the distal tip of the catheter 10. The balloon 26 is inflated and deflated through a fourth lumen 28 for stabilizing the position of the catheter tip after its insertion in the bloodstream.

Figure 2:
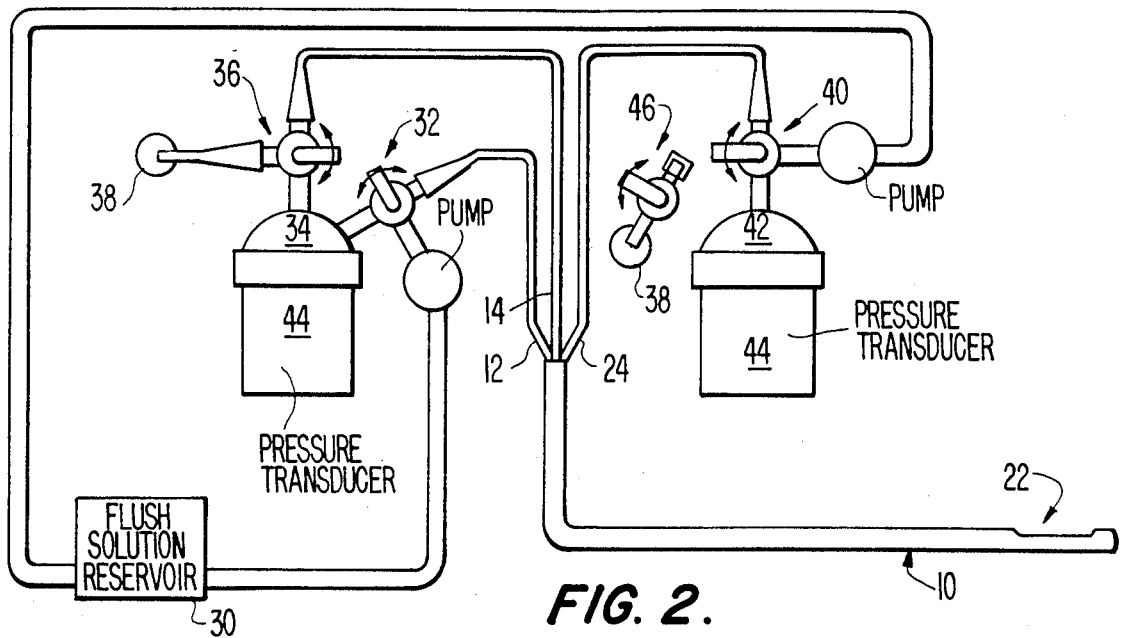
FIG. 2 is a schematic diagram of apparatus in accordance with the present invention.

With reference now to FIG. 2, first and third lumens 12, 24 of the catheter 10 are connected to a flush solution reservoir which supplies physiologically normal saline solution to the lumens under pressure to fill and flush the lumens. The pressure of the solution is pulsed by a piezo-electric transducer at 0.5 to 12 W and 10 Khz to 20 Mhz to provide a scrubbing action in the fibrils 16, which prevents blockage and erythrocyte contamination of the surfaces of the fibrils 16 by loosening material that collects on them. The surfaces of the fibrils are also flushed with fluid from the third lumen 24 every thirty minutes to remove debris and prevent thrombic activity from blocking the port area 22.

The catheter and other tubing is selected so as to have a natural resonance frequency low enough to prevent the ultrasonic scrubbing from interfering with pressure measurements.

The first lumen 12 is connected to the supply reservoir 30 by a first T-valve 32 which alternatively connects the first lumen 12 to a first access port of the osmotic pressure transducer dome 34. The second lumen 14 is normally connected by a second T-valve 36 to a second access port of the first pressure transducer dome 34 or, alternately, to an air filter 38 which prevents contamination of the saline. The third lumen 24 is connected by a third T-valve 40 alternatively to the supply reservoir 30 or to the first access port of a hydrostatic pressure transducer dome 42. The second port of the hydrostatic pressure transducer dome 42 is normally closed to the air by a fourth T-valve 46, but can be opened to the air through an air filter 38.

The pressure transducer domes are each provided with a high-sensitivity (50 wv/mm H$_2$O) pressure transducer capsule 44. Care must be exercised to assure that the two transducers 34, 42 are at the same level and in the same horizontal plane as the catheter port 22 while monitoring a patient or calibrating the device.

Figure 1A:
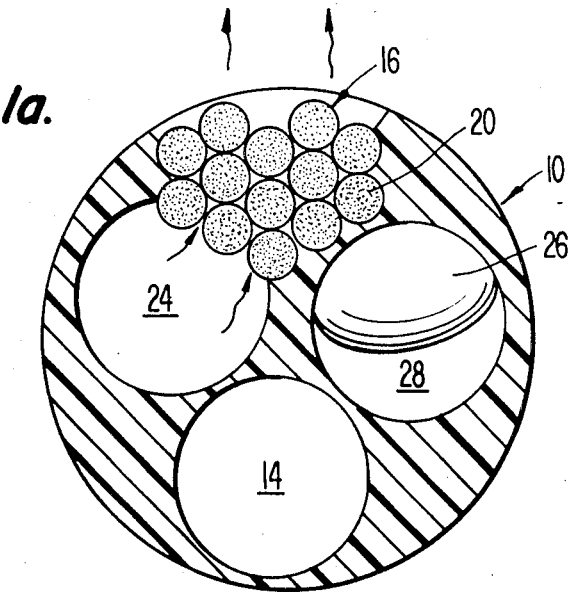
FIG. 1a is a cross section of the catheter means taken at "1a" in FIG. 1.

With reference again to FIG. 1a, to monitor the intravascular colloidal osmotic (oncotic) pressure affecting lung tissue in accordance with the present invention, the apparatus is filled with saline and calibrated. Then the catheter 10 is inserted into a pulmonary artery and the flotation balloon 26 near the tip with the catheter is inflated. The buoyancy of the balloon 26 moves the balloon 26 and the catheter 10 toward a wall of the artery. Contact with a wall of the artery helps to maintain a stable relation between the catheter port 22 at the distal end of the catheter 10 and the bloodstream in the artery.

The pressure transducers are calibrated before the catheter is inserted by submerging the catheter port 22 in a 25% of colloidal suspension of human albumin. The apparatus is filled, and flushed with physiologically normal saline to remove any trapped air from the system. After three minutes' submersion in the albumin suspension the transducers 44 are calibrated as follows:

1. The transducers 44 are zeroed;
2. The pressure transducer domes 34, 42 are opened to ambient air pressure through T-valves 36 and 46;
3. An offset value ($A^1$) is read from each transducer 44 and recorded; and
4. The T-valves are then adjusted so that the pressure transducer domes 34, 42 are connected only to the lumens 12, 14, and 24.

About five minutes after the catheter has been secured in place in the pulmonary artery, the fluid has reached an equilibrium such that monitoring can begin. Thereafter while the catheter 10 remains in place the readings $A_h$ of the hydrostatic pressure transducer 42 and $A_o$ of the osmotic pressure transducer are subtracted from the $A^1$ value recorded for these transducers, respectively, to determine the pressure P on each transducer, which is generally stated as:

$$P = A^1 - A$$

The intravascular COP value is then:

$$COP_v = P_o + P_h$$

The two-ended osmometer lumen in accordance with the present invention permits flushing of a sterilized catheter, to remove trapped air immediately before insertion of the catheter, which eliminates the need to store sterilized catheters in a humidity saturated environment. This osmometer also is adapted for percutaneous insertion, without the use of cut down insertion methods required by other osmometers. Furthermore, the use of multiple, fiber-filled lumens in the preferred embodiment greatly increases the ratio surface area relative to fluid volume. This increase reduces equilibration time, thereby making the use of longer catheters possible and permitting more convenient insertion.

The embodiment described above is one example of apparatus in accordance with the present invention and many variations and modifications are possible within the spirit and scope of this invention. For example, hydrostatic pressure $P_h$ may be determined by separate means and then normalized in order to determine $COP_v$ in accordance with the present invention, or the catheter port may be located along the length of the catheter at a point away from the tip of the catheter. Also, if the pressure indicator provides negative as well as positive readings there is no need for immersing the catheter in an albumin solution for the zeroing procedure. The pressure transducers 44 can then be zeroed immediately by opening the pressure transducer domes 34 and 42 to air. In the equation, the offset value $A'$ becomes equal to zero and $P = -A$. In such a case the COP becomes then:

$$COP_v = P + P_h$$

Furthermore, one or more fibrils of polysulfane or polyacrylonitrile copolymers or a specially treated cellulose acetate may be used in place of the six fibrils described above.

We claim:
1. Apparatus for use in a system for measuring osmotic pressure in a bloodstream, said apparatus comprising:
   catheter means for insertion in a subject's bloodstream, said catheter means having first and second lumens therein and a port adapted to permit contact of the interior of said catheter with said bloodstream;

at least one tube of a material that is semi-permeable to a fluid of said bloodstream, said tube fluidly connecting said first lumen with said second lumen and extending across said port, the ends of said tube being connected to said first and second lumens, respectively, in airtight and watertight seals; and a pressure sensor means for measuring the pressure in said first lumen.

2. Apparatus for measuring osmotic pressure, said apparatus comprising:

catheter means for insertion in a subject's bloodstream, said catheter means having three lumens, and a port adapted to permit passage of fluid from said bloodstream into said catheter means;

at least one tube of a material that is semi-permeable to said fluid from said bloodstream, said tube fluidly connecting a first lumen with a second lumen and extending across said port, the ends of said tube being connected to said first and second lumens, respectively, in airtight and watertight seals;

the third lumen being in fluid communication with the exterior of said tube opposite said port;

a first pressure sensor means for measuring the pressure of fluid in said first lumen; and a second pressure sensor means for measuring the pressure of fluid in the third lumen, said third lumen opening to the bloodstream at said port.

3. Apparatus for measuring osmotic pressure, said apparatus comprising:

catheter means for insertion in a subject's bloodstream, said catheter means having three lumens and a port adapted to permit contact of the interior of said catheter with said bloodstream;

at least one tube of material that is semi-permeable to a fluid of said bloodstream fluidly connecting a first lumen with a second lumen and extending across said port, the ends of said tube being connected to said first and second lumens, respectively, in an airtight and watertight seal, said material being permeable to substances having a molecular weight not greater than 30,000; the third lumen being in fluid communication with the exterior of said tube opposite said port;

a first pressure sensor means for measuring the pressure in said first lumen; and a second pressure sensor means for measuring the pressure in the third lumen, said third lumen opening to said bloodstream at said port.

4. Apparatus as claimed in claim 1, 2 or 3 wherein said apparatus further comprising value means for selectively connecting said third lumen to a source of fluid pressure for flushing fluid past said tube to remove debris.

5. Apparatus as claimed in claim 1, 2 or 3 wherein said tube is filled with fibers, said tube having a fluid volume which is reduced by said fibers, with said fibers providing support for said tube against external pressure.

6. A method for measuring osmotic pressure in the bloodstream comprising the steps:

inserting a multiple-lumen catheter into the circulatory system of a subject, said catheter having first, second, and third lumens filled with a physiologically normal fluid and having said first and second lumens fluidly connected by at least one semipermeable tube extending across a port in said catheter, and a third lumen in communication with the exterior of said tube opposite said port;

measuring the fluid pressure in said first lumen;

measuring the fluid pressure in said third lumen; and adding the pressure of the fluid in the first lumen to the pressure of the fluid in the third lumen to determine the intravascular osmotic pressure.

7. A method as claimed in claim 6 further comprising the step of periodically flushing a physiologically normal fluid through said third lumen past said tube to prevent thrombic activity from interfering with the measurement of osmotic pressure.

* * * * *

UNITED STATES PATENT AND TRADEMARK OFFICE
CERTIFICATE OF CORRECTION

PATENT NO. : 4,603,699
DATED : August 5, 1986
INVENTOR(S) : Jacques M. Himpens

It is certified that error appears in the above–identified patent and that said Letters Patent are hereby corrected as shown below:

Column 6, line 12, "value" should read --valve--.

Signed and Sealed this

Fourth Day of November, 1986

[SEAL]

Attest:

DONALD J. QUIGG

Attesting Officer

Commissioner of Patents and Trademarks